United States Patent
Ray et al.

(10) Patent No.: US 10,031,059 B1
(45) Date of Patent: Jul. 24, 2018

(54) CONTROLLED SAMPLING VOLUME OF CLOUDS FOR MEASURING CLOUD PARAMETERS

(71) Applicant: Rosemount Aerospace Inc., Burnsville, MN (US)

(72) Inventors: Mark Ray, Burnsville, MN (US); Kaare Josef Anderson, Farmington, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

(21) Appl. No.: 15/411,520

(22) Filed: Jan. 20, 2017

(51) Int. Cl.
| | |
|---|---|
| *G01N 15/02* | (2006.01) |
| *G01W 1/00* | (2006.01) |
| *G01N 15/06* | (2006.01) |
| *G01N 21/49* | (2006.01) |

(52) U.S. Cl.
CPC ......... *G01N 15/0211* (2013.01); *G01N 15/06* (2013.01); *G01W 1/00* (2013.01); *G01N 21/49* (2013.01); *G01N 2015/0693* (2013.01)

(58) Field of Classification Search
CPC .... G01N 21/49; G01N 21/21; G01N 15/1413; G01N 2201/0697; G01N 2201/06113; G01N 2201/12; G01N 2021/4792; G01N 15/0211; G01N 15/06; G01N 2015/0693; B64D 15/20
See application file for complete search history.

(56) References Cited

U.S. PATENT DOCUMENTS

| | | | | |
|---|---|---|---|---|
| 4,722,599 | A * | 2/1988 | Fruengel | G01S 17/107 342/26 D |
| 6,567,586 | B2 | 5/2003 | Brophy et al. | |
| 6,839,485 | B2 | 1/2005 | Gardner et al. | |
| 7,026,600 | B2 | 4/2006 | Jamieson et al. | |
| 8,144,325 | B2 * | 3/2012 | Ray | B64D 15/20 356/342 |
| 8,338,785 | B2 | 12/2012 | Ray | |
| 9,476,968 | B2 * | 10/2016 | Anderson | G01M 11/00 |
| 2006/0126055 | A1 * | 6/2006 | Meneely | G01C 5/005 356/28.5 |

(Continued)

*Primary Examiner* — Sang Nguyen
(74) *Attorney, Agent, or Firm* — Kinney & Lange, P.A.

(57) ABSTRACT

Apparatus and associated methods relate to determining a size and/or density of Super-cooled Large Droplets (SLDs) in a cloud atmosphere by comparing detected optical signals reflected from small and large sampling volumes of a cloud atmosphere. In some embodiments, an optical pulse is generated and divergently projected from a first optical fiber. A collimating lens is aligned within the divergently projected optical pulse collimating a portion thereof. The collimated and uncollimated portions of the optical pulse are projected into the small and large sampling volumes of the cloud atmosphere, respectively. The ratio of the collimated to the uncollimated portions can be optically controlled. Signals corresponding to optical pulses having different collimated/uncollimated ratios are backscattered by the cloud atmosphere, detected and compared to one another. A processor is configured to calculate, based on scintillation spike differences between the optical pulses of different collimated/uncollimated ratios, a size and/or density of SLDs.

20 Claims, 4 Drawing Sheets

(56) References Cited

U.S. PATENT DOCUMENTS

| | | | |
|---|---|---|---|
| 2007/0210254 A1* | 9/2007 | Killinger | G01N 21/3504 250/338.5 |
| 2008/0264164 A1* | 10/2008 | Solheim | G01J 5/02 73/170.27 |
| 2010/0110431 A1* | 5/2010 | Ray | B64D 15/20 356/342 |
| 2011/0019188 A1* | 1/2011 | Ray | B64D 15/20 356/342 |
| 2011/0220779 A1* | 9/2011 | Takaoka | H01S 5/02284 250/216 |
| 2012/0104225 A1* | 5/2012 | McEldowney | G01J 1/0228 250/205 |
| 2015/0070700 A1* | 3/2015 | Ray | G01S 17/95 356/342 |

* cited by examiner

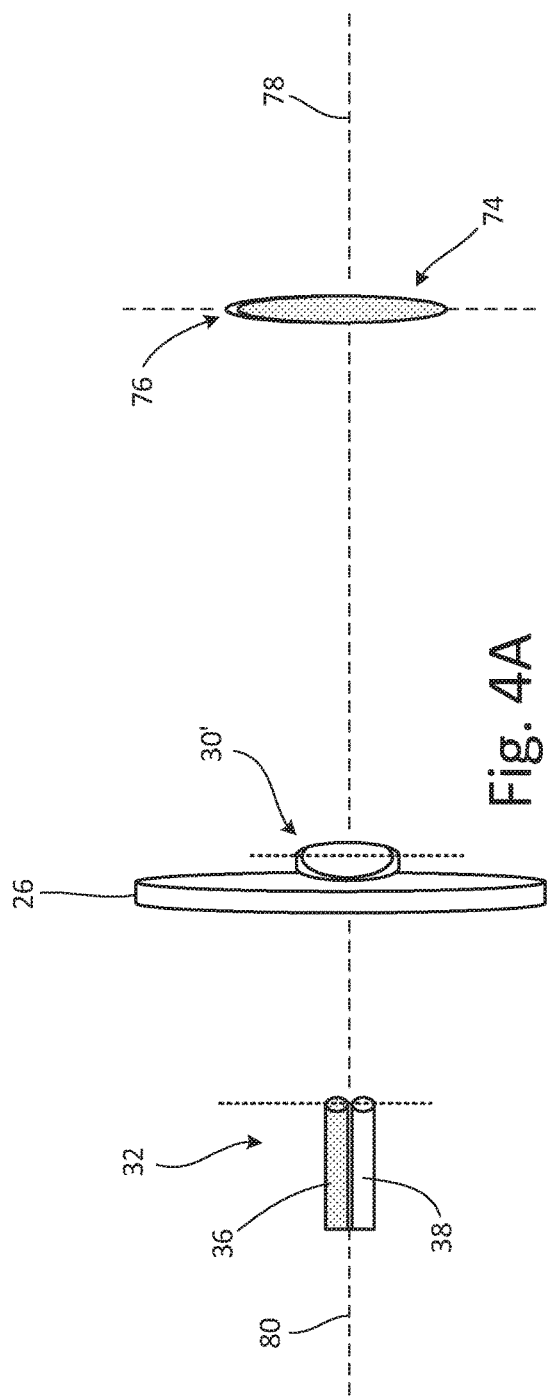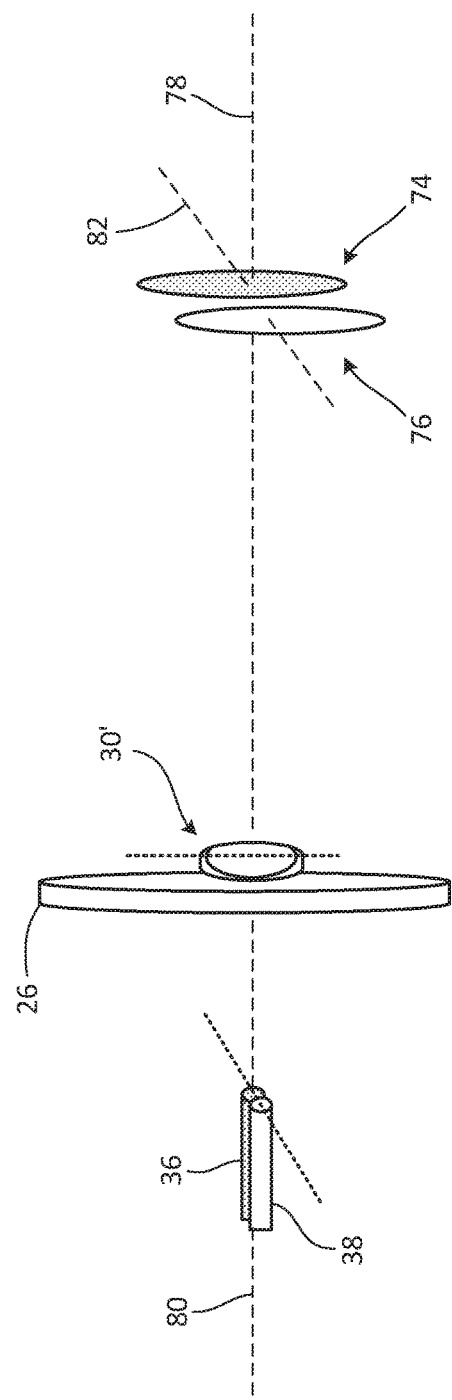

CONTROLLED SAMPLING VOLUME OF CLOUDS FOR MEASURING CLOUD PARAMETERS

BACKGROUND

Various cloud conditions can present risks to aircraft when traveling through them. If the temperature of a cloud atmosphere is below the freezing point for water, water droplets can become super-cooled liquid droplets. These super-cooled liquid droplets can then undergo a liquid-to-solid phase change upon impact with an aircraft surface. Ice accretes at different surface regions for different sizes of the super-cooled liquid droplets in the cloud atmosphere. Thus, characterizing the sizes of super-cooled water droplets in a cloud atmosphere can facilitate prediction of surface regions where ice will accrete as well as providing alerts of potentially dangerous conditions to a pilot.

Super-cooled small water droplets tend to form ice only on leading edges of an aircraft's exterior surface. Super-cooled Large water Droplets (SLDs), however, can strike the leading edge of a wing and run back past the icing protection systems, or can traverse airflow vectors and strike surfaces aft of these leading edges. Ice that forms on unprotected surface regions can severely alter the aerodynamics of the aircraft. Such ice accretion may cause aircraft stall or result in unpredictable aircraft control variation that might lead to flight issues. When in a cloud, ice can form on control surfaces and/or lift surfaces.

Not every cloud, however, has a significant SLD population. Different clouds and different atmospheric conditions may be accompanied by various water droplet size distributions, different ice/liquid ratios, etc., some of which may be entirely safe to an aircraft, while others may not be safe. Such water droplet size distributions and ice/liquid ratios may be measured as cloud metrics using various types of instruments.

Some aircraft are equipped with Light Detection and Ranging (LIDAR) systems to measure cloud metrics. Such systems can characterize clouds that have water droplets that have a size distribution having a single mode. Either the mean droplet size or the mode droplet size can be calculated by inversion of a backscatter signal using such systems. These systems can also calculate the density of water droplets for such mono-modal distributions.

Multi-modal distributions of water droplet sizes, however, can be difficult to characterize. Such multi-modal distributions may occur, for example, when cumulus clouds drop drizzle or rain into a lower stratiform cloud deck, creating icing conditions. For droplet size distributions having a dominant mode and a secondary mode (e.g. large distribution of relatively small water droplets plus a small distribution of large water droplets), it can be difficult to detect the anomalous amounts of large water droplets in the secondary mode.

LIDAR systems project pulses of a collimated laser beam into the cloud atmosphere and then sense the signal backscattered by the cloud atmosphere. The collimated laser beam samples a relatively small volume of the cloud, due to the collimated beam having a small field of view (e.g., 4 mrad of divergence is not atypical). Sampling such a small cloud volume can result in the beam encountering few, if any of the SLDs of a secondary distribution.

Depending on the size and density of the SLDs in the secondary distribution, the backscatter signal can appear as scintillation spikes superimposed on an otherwise smooth continuous range-resolved backscatter signal characteristic of the primary distribution. The size and frequency of occurrence of the scintillation spikes depends on the sizes of the SLDs and on the volume of space probed by the collimated laser beam.

Unlike the smooth range-resolved backscatter signal from the primary distribution, backscatter signals from small distributions of large droplet can have randomly occurring scintillation spikes. Averaging of such backscatter signals over multiple laser pulses, while boosting the signal-to-noise ratio of the sparse droplet contribution, can cause the sporadic scintillation spikes for the sparse large droplet distribution to be attenuated, and perhaps even fall below a noise floor. Thus, the SLDs, which can be hazardous to aircraft, may not be sensed.

Mono-modal distributions of SLDs can also be problematic, if the density of SLDs is small. Again, the backscatter signal can be characterized by scintillation spikes randomly located in the temporal stream of backscatter signals. Averaging of such backscatter signals can result in a signal amplitude that is small. Such a small signal may even fall below an instrument noise floor. Measurement techniques and instruments, which can more accurately characterize water droplet distributions, are needed.

SUMMARY

Apparatus and Associated methods relate to a system for measuring cloud parameters. The system includes a laser diode configured to generate a pulse of optical energy. The system includes a first optical fiber configured to transmit the generated pulse of optical energy and to divergently project, from a projection end, the transmitted pulse of optical energy over a first field-of-view determined by a first numerical aperture of the projection end. The system includes a collimating lens aligned within a subfield of the first field-of-view. The collimating lens is configured to collimate a narrow-field portion of the divergently projected pulse of optical energy refracted by the collimating lens into a narrow-field projection volume of a cloud atmosphere. A wide-field projection volume of the cloud atmosphere corresponds to a portion of the projected pulse not collimated by the collimating lens. The system includes a second optical fiber having a reception end aligned proximate and substantially parallel to the transmission end of the first optical fiber. The second optical fiber is configured to receive a portion of the projected pulse of optical energy reflected by the cloud atmosphere from within a second field of view determined by a second numerical aperture of the reception end. The second field-of-view includes narrow-field and wide-field reception volumes of the cloud atmosphere. The narrow-field reception volume corresponds to locations within the cloud atmosphere from which optical energy can be directed through the collimating lens and received by the second optical fiber. The wide-field reception volume corresponds to locations within the cloud atmosphere from which optical energy can be received by the second optical fiber not through the collimating lens. The system also includes a detector configured to detect and generate a signal indicative of the portion of the projected pulse of optical energy backscattered by the cloud atmosphere and received by the second optical fiber.

Some embodiments relate to a method for measuring cloud parameters. The method includes generating a pulse of optical energy. The method includes diverging the generated pulse of optical energy over a solid angle greater than a predetermined threshold. The method includes collimating a portion of the divergent pulse of optical energy and projecting the collimated portion into a first projection volume of a cloud atmosphere. The method includes projecting an uncollimated portion of the divergent pulses of optical energy into a second projection volume of the cloud atmosphere. The method includes receiving optical energy from a first reception volume of the cloud atmosphere, the first reception volume intersecting the first projection volume. The method includes receiving optical energy from a second reception volume of the cloud atmosphere, the second reception volume intersecting the second projection volume. The method also includes detecting and generating a signal indicative of combined collimated and uncollimated portions backscattered by the cloud atmosphere from within the intersections of the first and second projection volumes and the first and second reception volumes, respectively.

BRIEF DESCRIPTION OF THE DRAWINGS

FIGS. 4A-4B are schematic diagrams that illustrate the relationship between the sampling volume and the relative orientation between a cylindrical lens and transmitter/receiver fiber orientation.

DETAILED DESCRIPTION

Apparatus and associated methods relate to determining a size and/or density of Super-cooled Large Droplets (SLDs) in a cloud atmosphere by comparing detected optical signals reflected from small and large sampling volumes of a cloud atmosphere. In some embodiments, an optical pulse is generated and divergently projected from a first optical fiber. A collimating lens is aligned within the divergently projected optical pulse collimating a portion thereof. The collimated and uncollimated portions of the optical pulse are projected into the small and large sampling volumes of the cloud atmosphere, respectively. The ratio of the collimated to the uncollimated portions can be optically controlled. Signals corresponding to optical pulses having different collimated/uncollimated ratios are backscattered by the cloud atmosphere, detected and compared to one another. A processor is configured to calculate, based on scintillation spike differences between the optical pulses of different collimated/uncollimated ratios, a size and/or density of SLDs.

Apparatus and associated methods relate to sampling both large and small volumes of a cloud atmosphere. Sampling a large volume of a cloud atmosphere facilitates obtaining a large signal response from even a sparse distribution of water droplets in the cloud atmosphere. Such a large volume can be probed by projecting an uncollimated optical beam into the cloud atmosphere and sampling the signal backscattered from the water droplets located within the probed volume. Sampling a small volume of a cloud atmosphere complements the large volume sampling and facilitates quantization of various metrics of the cloud atmosphere. A small volume can be probed by projecting a collimated optical beam into the cloud atmosphere.

The uncollimated optical beam can be generated by projecting a pulse of light energy from an end of a first optical fiber. The pulse of light energy can be projected from a polished surface of the first optical fiber, for example, without having a lens between the end of the optical fiber and the cloud atmosphere. The unlensed beam can diverge as it projects from the end of the first optical fiber. Various metrics can be used to characterize the divergence of the projected optical beam. For example, angle of divergence ($\theta$), numerical aperture (NA), focal ratio (F/#), and solid angle ($\Omega$) can all be used as metrics characterizing the divergence of the projected optical beam.

Figure 1:
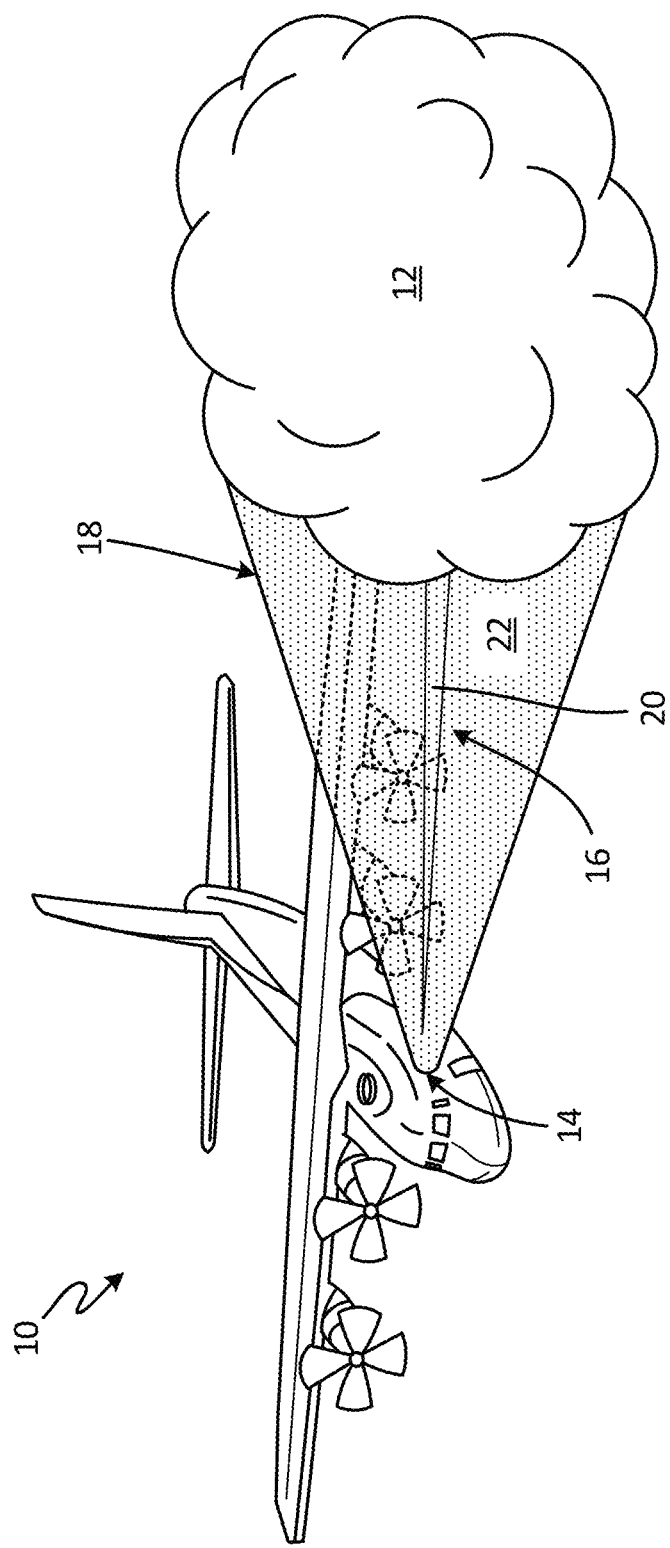
FIG. 1 is a schematic view of an aircraft using an exemplary cloud conditions measurement system using both a collimated portion and an uncollimated portion of pulses of optical energy.

FIG. 1 is a schematic view of an aircraft using an exemplary cloud conditions measurement system using both a collimated portion and an uncollimated portion of each pulse of optical energy. In FIG. 1, aircraft 10 is traveling through cloud atmosphere 12. Aircraft 10 is equipped with cloud conditions measurement system 14 that is probing cloud atmosphere 12 with collimated portion 16 and uncollimated portion 18 of each pulse of optical energy.

Collimated portion 16 of each pulse of optical energy has a relatively small divergence and is projected into first projection volume 20 of cloud atmosphere 12. In some embodiments, the divergence of collimated portion 16 can be characterized by an angle of divergence of 4 mrad, for example. An exemplary cloud atmosphere, which is sampled over a depth of ten meters by such a collimated optical beam, results in a first probe volume 20 being equal to about $5 \times 10^{-3}$ m$^3$.

Uncollimated portion 18 has a relatively large divergence and is projected into second projection volume 22. In some embodiments, the divergence of uncollimated portion 18 can be a result of projection from an optical fiber having a numerical aperture of 0.39, for example. An exemplary cloud atmosphere, which is sampled over a depth of ten meters by such an uncollimated optical beam results in second probe volume 22 being equal to about 170 m$^3$. Thus, second probe volume 22 is more than thirty-thousand times larger than first probe volume 20.

Each of the collimated and uncollimated portions 16 and 18 can be backscattered by water droplets and ice crystals of cloud atmosphere 12. The optical energy backscattered by cloud atmosphere 12 can be detected by one or more optical detectors. The detector can then generate electrical signals corresponding to the detected optical energy so backscattered by cloud atmosphere 12. The generated electrical signals are indicative of various metrics of cloud atmosphere 12.

If only the uncollimated portion of the optical energy beam is projected into and backscattered by cloud atmosphere 12, a relatively large volume of cloud atmosphere 12 from which water droplets backscatter the pulses of optical energy is sampled. This large volume is likely to have water particles distributed fairly uniformly throughout the sampled volume. Even should the particle density be relatively modest, such a large sample volume would likely have many particles well distributed throughout the range distances from the optical source. When large volumes of cloud atmosphere 12 are sampled using such an uncollimated LIDAR system, backscattering results from a great many water droplets, which are encountered at many range locations from the location where the pulses of optical energy are emitted. The corresponding backscatter signal that is generated when sampling such a large volume will be a smooth continuous range-resolved backscatter signal, with the range corresponding to photonic round-trip flight time (e.g., time for light to travel from an optical source to a backscattering water droplet within the sampling volume, plus the return time to an optical detector).

If, however, only the collimated portion of the optical energy beam were projected into and backscattered by cloud atmosphere 12, a relatively small volume of cloud atmosphere 12 is sampled. When small volumes of cloud atmosphere 12 are sampled using such a collimated LIDAR system, backscattering results from the relatively rare photonic encounter with a water droplet. Each backscattering event is encountered at a specific range location from the location where the pulses of optical energy are emitted. The corresponding backscatter signal that will be generated when sampling such a small volume will be a series of scintillation spikes generated at each photonic round-trip flight time.

In such small-sample-volume scenarios, the generated signal indicative of various cloud metrics can be marked with scintillation spikes, each corresponding to a photonic round trip flight time to and from a particular water droplet. Even when probing small sample volumes, many, if not most, clouds have so many small droplets distributed throughout the sampling volume that the generated backscatter signal is relatively smooth and continuous. Scintillation spikes usually result from Super-cooled Large Droplets (SLDs). SLDs are often found in clouds having a bimodal distribution, with the primary mode including small droplets. In such bimodal cloud scenarios, the signal detected when sampling small volumes of bimodally-distributed water droplets can have scintillation spikes superimposed upon a smooth continuous range-resolved backscatter signal. The scintillation spike portion of the backscatter signal principally results from SLD backscattering, while the smooth continuous portion of the backscatter signal results from backscattering from small but densely-distributed droplets.

Thus, obtaining signals facilitating the isolation of both the smooth continuous and the scintillation-spike portions of the backscatter signal can facilitate determination of metrics of both the primary-mode droplets and the secondary-mode droplets.

Figure 2:
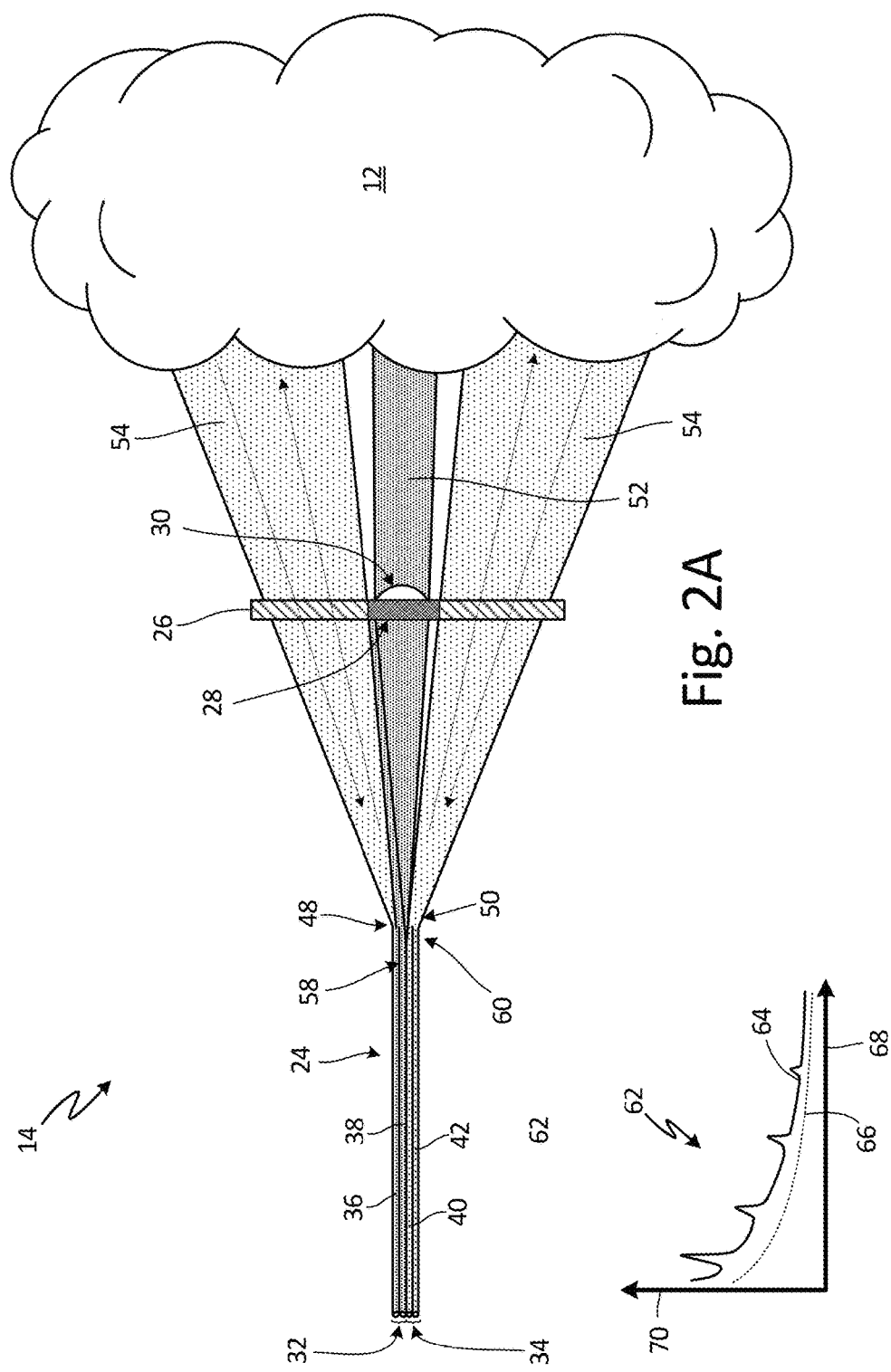
FIG. 2A is a schematic diagram of an embodiment of a cloud conditions measurement system generating both collimated and uncollimated portions of a light beam.
FIG. 2B is a graph of exemplary backscatter signals resulting from both collimated and uncollimated portions of a light beam.

FIG. 2A is a schematic diagram of an embodiment of a cloud conditions measurement system that generates both collimated and uncollimated portions of pulses of optical energy (e.g., light beams). In FIG. 2A, cloud conditions measurement system 14 is depicted probing cloud atmosphere 12. Cloud conditions measurement system 14 includes fiber bundle 24, window 26, optical filter 28, and collimating lens 30. In the depicted embodiment, fiber bundle 24 includes two transmitter/receiver pairs 32 and 34 of fibers. First transmitter/receiver pair 32 can be configured to transmit, via first transmitter fiber 36, and receive, via first receiver fiber 38, optical energy of a first wavelength, for example. Second transmitter/receiver pair 34 can be configured to transmit, via second transmitter fiber 40, and receive, via second receiver fiber 42, optical energy of a second wavelength.

Pulses of optical energy are generated by an optical source (not depicted) and transmitted via first and/or second transmitter fibers 36 and 40 and divergently projected from transmitter ends 48 and 50, respectively. Measures of divergence of the divergently projected pulses of optical energy can be determined by a numerical aperture (NA) of the projection ends 48 and 50. In some embodiments, the NA of the projection ends 48 and 50 are substantially equal to one another. In some embodiments the NA of the projection ends 48 and 50 are dissimilar from one another.

Window 26 is aligned with the divergently projected pulses of optical energy. Filter 28 is aligned with a center region of window 26 in the depicted embodiment. Filter 28 is depicted as transmitting a centrally-projected portion of divergently projected pulses of optical energy of the first wavelength and absorbing a centrally-projected portion of divergently projected pulses of optical energy of the second wavelength. In some embodiments, filter 28 is a bandpass filter that, for example, transmits optical energy of the first wavelength and absorbs optical energy of a second wavelength. In some embodiments, transmission and absorption of optical pulses can be controlled in other ways. For example, a shutter can be controlled to pass or block pulses projected at different times. In some examples, LCD technology can provide electrical control of light absorption Collimating lens 30 is aligned with a center region of window 26 and with filter 28 in the depicted embodiment. Collimating lens 30 is depicted as collimating the centrally-projected portion of divergently projected pulses of optical energy of the first wavelength and directing the collimated portion into a first projection volume 52 of cloud atmosphere 12. Portions not collimated by collimating lens 30 of divergently projected pulses of optical energy of the first wavelength are projected into a second projection volume 54 of cloud atmosphere 12. Similarly portions not absorbed by filter 28 of divergently projected pulses of optical energy of the second wavelength are projected into third projection volume (e.g., third projection volume is approximately the same as second projection volume 54) of cloud atmosphere 12.

The portions of pulses of optical energy projected into each of the projection volumes 52 and 54 can be backscattered by cloud atmosphere 12. The collimated portion of each of the optical energy pulses of the first wavelength projected into first projection volume 52 can be approximately ray-traced back upon its projection path and then focused by collimating lens 30 onto receiver end 58 of receiver fiber 38. The uncollimated portion of each of the optical energy pulses of the first wavelength projected into second projection volume 54 can be approximately ray-traced back upon its projection path and is also received by receiver end 58 of receiver fiber 38. Similarly, the uncollimated portions of optical energy pulses of the second wavelength projected into third projection volume can be approximately ray-traced back upon its projection path and is received by receiver end 60 of receiver fiber 42.

Both collimated and uncollimated portions of the pulses of optical energy are received and subsequently detected by an optical detector (not depicted). The uncollimated portions are projected into projection volume 54, which is comparatively large with respect to projection volume 52 into which the collimated portion is projected. The relatively large sampling volume (i.e., the portion of the projection volume that contributes to a detectable signal of the projected optical energy backscattered by the cloud atmosphere) ensures that virtually all of the droplets in the cloud, small or large, are illuminated, and from which photons are backscattered and subsequently detected. Sampling such a large number of droplets results in a smooth, continuous range-resolved backscatter signal. Even should the cloud have a bimodal distribution of droplet sizes, the contribution of large droplets may still be too small to result in a backscatter signal that can be differentiated from one caused by a monomodal small-droplet cloud.

Conversely, the collimated portion is projected into projection volume 52, which is comparatively small; with respect to projection volume 54 onto which the uncollimated portions are projected. The relatively small sampling volume ensures that a relatively modest number of droplets in the cloud, small or large, are illuminated and their backscatter detected. Sampling such a small number of droplets results in a scintillation spikes superimposed on an otherwise smooth, continuous, range-resolved backscatter signal. A cloud that has a bimodal distribution of droplet sizes can thereby be differentiated, via the scintillation spikes, from a monomodal small-droplet cloud.

FIG. 2B is a graph of exemplary backscatter signals resulting from both collimated and uncollimated portions of a light beam. In FIG. 2B, graph 62 includes two range-resolved backscatter signals 64, 66. First range-resolved backscatter signal 64 corresponds to a projected pulse of optical energy having both collimated and uncollimated portions. Second range-resolved backscatter signal 66 corresponds to a projected pulse of optical energy having only an uncollimated portion. Graph 62 has horizontal axis 68, which is indicative of range within cloud atmosphere 12 from which the projected optical energy is backscattered. Graph 62 has vertical axis 70, which is indicative of intensity of the detected backscatter signal. Note that backscatter signal 64 includes scintillation spikes corresponding to the collimated portions of the projected pulses of optical energy. Note also that backscatter signal 66 has no scintillation spikes due to the absence of signal contribution corresponding to a collimated sampling volume.

Figure 3:
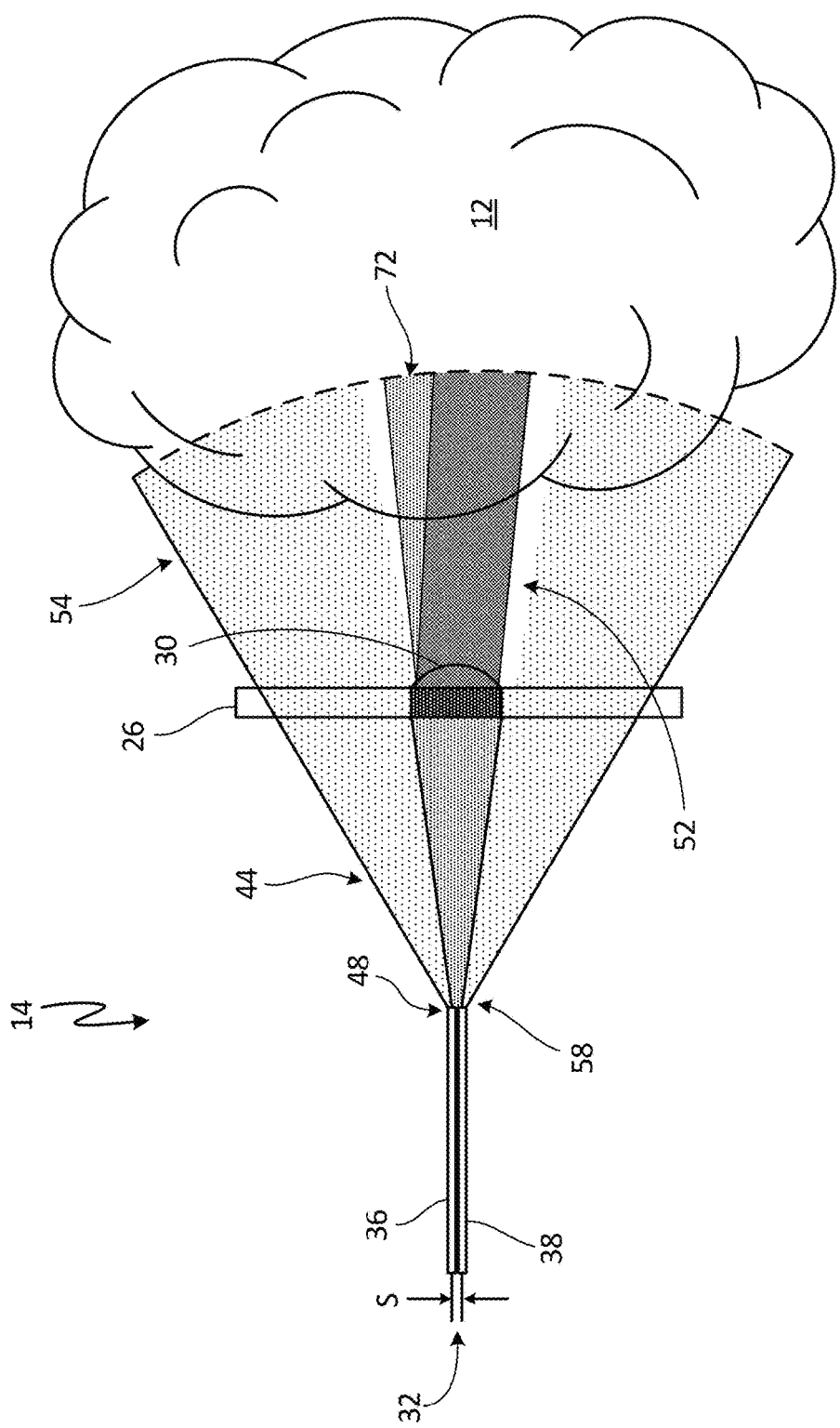
FIG. 3 is a schematic diagram that illustrates the relationship between the projected field of view and the received field of view for adjacent fibers sharing a common lens.

FIG. 3 is a schematic diagram that illustrates the relationship between the projector field of view and the receiver field of view for adjacent fibers sharing a common lens. In FIG. 3, cloud conditions measurement system 14 is depicted probing cloud atmosphere 12. Only first transmitter/receiver fiber pair 32 is depicted, so as to permit the collimated and uncollimated portions of divergent optical-energy pulses produced by a first optical source to be depicted unobscured by the uncollimated portion of each divergent optical-energy pulse (depicted in FIG. 2A) by a second optical source.

Some embodiments include a processor to receive backscatter signals 64 and 66. The processor can be configured to calculate, based on the received backscatter signals 64 and 66, metrics of cloud atmosphere 12. The processor can be configured, for example, calculate a density and or an average size of SLDs in the cloud atmosphere based on the smooth continuous backscatter signal 66. The processor can be configured to calculate a density and/or a size metric based on the scintillation spikes of backscatter signal 64. For example, in some embodiments, the size of a scintillation spike can be indicative of a size of a SLD. In some embodiments, a frequency and/or density of scintillation spikes along the horizontal axis time 112 (e.g., time or range) axis can be indicative of a density of SLDs. In some embodiments, processor can use both backscatter signals 64 and 66 to calculate metrics of a bimodal distribution of water droplets in cloud atmosphere 12.

In FIG. 3, transmitter fiber 36 has transmitter end 48 is aligned proximate and substantially parallel to receiver end 58 of receiver fiber 38. Transmitter fiber 36 transmits pulses of optical energy and divergently projects the transmitted pulses from transmitter end 48. Each of the divergent pulses has two portions: i) a collimated portion projected into projection volume 52; and ii) an uncollimated portion projected into projection volume 54. The collimated portion is the portion of a divergent pulse of optical energy that is collimated by collimator lens 30. The uncollimated portion is the portion of a divergent pulse of optical energy that is not collimated by collimator lens 30. In this way, both the collimated and the uncollimated portions are complementary to one to another.

The collimated portion is projected by collimator lens 30 into first projection volume 52. The uncollimated portion is divergently projected by transmitter end 48, through window 26, and into cloud atmosphere 12. Because transmitter end 48 and receiver end 58 are adjacent to one another, albeit close to one another, first reception volume 72 of cloud atmosphere from which light is focused on receiver end 58 is not exactly the same volume as first projection volume 52. First reception volume 72 corresponds to the field of view of receiver end 58 or receiver fiber 38 as imaged by collimator lens 30. At range locations that are nearby or close to collimator lens 30, first projection volume is substantially coextensive with first reception volume 72. But as the range location becomes more distal from collimator lens, first projection volume 52 and first reception volume 72 diverge from one another. At a specific range location, the intersection between first projection volume 52 and first reception volume 72 becomes non-existent.

Such a range at which the intersection of first projection volume 52 and first reception volume 72 becomes zero can be mathematically determined. Using a spherical collimating lens 30 and assuming that the collimated portions of projected optical energy pulses are well-collimated with approximately no divergence, the separation is approximately:

$$R = (L-S)\left(\frac{f}{S-d}\right)$$

Here, R is the calculated range at which no intersection of first projection volume 52 and first reception volume 72 begins. L is the diameter and f is the focal length of collimating lens 30. S is center-to-center separation between transmitter and receiver ends 48 and 58 of transmitter and receiver fibers 36 and 38, respectively. And d is the diameter of the transmitter and receiver fibers 36 and 38. For example, if L=6 mm, f=25 mm, S=300 μm, and d=250 μm, then R is calculated to be 2.85 meters.

For some cloud atmospheres, such a small range can result in too few Super-cooled Large Droplets to be distributed therein for adequate measurement. For such cloud atmospheres, sampling volumes that are larger than the above calculated one, and yet smaller than sampling volumes 54 and 56 can be desirable for use in determining metrics of SLDs.

FIGS. 4A-4B are schematic diagrams that illustrate the relationship between the sampling volume and the relative orientation between a cylindrical lens and transmitter/receiver fiber orientation. In FIGS. 4A-4B, window 26, instead of having a spherical collimating lens, has a cylindrical collimating lens 30'. In FIGS. 4A-4B, transmitter/receiver fiber pair 32 is axially aligned with window 26, cylindrical collimating lens 30', and projected fields of view 74 and 76 along central axis 78. Projected field of view 74 corresponds to transmitter fiber 36 of transmitter/receiver fiber pair 32. Projected field of view 76 corresponds to receiver fiber 38 of transmitter/receiver fiber pair 32. Projected fields of view 74 and 76 are elliptical instead of spherical, because collimating lens 30' is cylindrical instead of spherical. Cylindrical collimating lens 30' has high curvature in a transverse direction and low curvature in a longitudinal direction. Such astigmatic curvature causes the elliptical fields of view 74 and 76 to have a long extent in the longitudinal direction and a short extent in the transverse direction.

In FIG. 4A, projected fields of view 74 and 76 are displaced from one another along longitudinal axis 80, which is caused by the separation distance S between transmitter fiber 36 and receiver fiber 38. Because transmitter fiber 36 and receiver fiber 38 are separated in a direction parallel to longitudinal axis 80, fields of view 74 and 76 are also displaced from one another along the longitudinal axis 80. Because the fields of view 74 and 76 are relatively extensive in the longitudinal direction, the intersection of the transmitter and receiver fields of view 74 and 76 is large (e.g., much greater than 50% of each field of view).

In FIG. 4B, transmitter and receiver fibers 36 and 38 are rotated with respect to optical axis 78. Transmitter and receiver fibers 36 and 38 are aligned parallel to transverse axis 82 in FIG. 4B. Transverse axis 82 is orthogonal to both optical axis 78 and longitudinal axis 80. Because the separation between transmitter and receiver fibers 36 and 38 is in a direction parallel to transverse axis 82 (e.g., in a transverse direction), fields of view 74 and 76 are displaced one from another along transverse axis 82. In the depicted schematic, fields of view 74 and 76 are displaced such that no intersection remains between fields of view 74 and 76. Thus, the intersection between fields of view 74 and 76 is a function of the relative orientation of the transmitter/receiver fiber pair 32 and orientation of cylindrical collimating lens 30'.

The fields of view of the uncollimated portions corresponding to transmitter and receiver optical fibers 36 and 38 are much larger than for the collimated portions. Because the fields of view of the uncollimated portions are quite large, alignment of transmitter/receiver fibers 36 and 38 is not as important as for the collimated portions. Uncollimated portions corresponding to transmitter and receiver optical fibers 36 and 38 can be substantially equal or substantially the same so that the volume of the cloud atmosphere probed by a signal projecting from the first optical fiber is substantially the same volume from which a backscattered signal is received by the second optical fiber. Two fields of view, and any of the measures of divergence that characterize such fields of view, are substantially equal to one another if they differ by less than ten percent. For example if $2(\theta_2-\theta_1)/(\theta_2+\theta_1)<0.1$ then the two angles of divergence are substantially equal to each other.

The following are non-exclusive descriptions of possible embodiments of the present invention.

Apparatus and Associated methods relate to a system for measuring cloud parameters. The system includes a laser diode configured to generate a pulse of optical energy. The system includes a first optical fiber configured to transmit the generated pulse of optical energy and to divergently project, from a projection end, the transmitted pulse of optical energy over a first field-of-view determined by a first numerical aperture of the projection end. The system includes a collimating lens aligned within a subfield of the first field-of-view. The collimating lens is configured to collimate a narrow-field portion of the divergently projected pulse of optical energy refracted by the collimating lens into a narrow-field projection volume of a cloud atmosphere. A wide-field projection volume of the cloud atmosphere corresponds to a portion of the projected pulse not collimated by the collimating lens. The system includes a second optical fiber having a reception end aligned proximate and substantially parallel to the transmission end of the first optical fiber. The second optical fiber is configured to receive a portion of the projected pulse of optical energy reflected by the cloud atmosphere from within a second field of view determined by a second numerical aperture of the reception end. The second field-of-view includes narrow-field and wide-field reception volumes of the cloud atmosphere. The narrow-field reception volume corresponds to locations within the cloud atmosphere from which optical energy can be directed through the collimating lens and received by the second optical fiber. The wide-field reception volume corresponds to locations within the cloud atmosphere from which optical energy can be received by the second optical fiber not through the collimating lens. The system also includes a detector configured to detect and generate a signal indicative of the portion of the projected pulse of optical energy backscattered by the cloud atmosphere and received by the second optical fiber.

A further embodiment of the foregoing system can further include a processor configured to calculate, based on the generated signal, a metric of SLDs.

A further embodiment of any of the foregoing systems, wherein the calculated metric can be a size and/or density of SLDs.

A further embodiment of any of the foregoing systems, wherein the collimator lens can be a spherical lens.

A further embodiment of any of the foregoing systems, wherein the collimator lens can be a cylindrical lens.

A further embodiment of any of the foregoing systems, wherein a relative orientation of the cylindrical lens with respect to an orientation of a juxtaposition of the transmission and reception ends, or the first and second optical fibers, respectively, can be configured such that an intersection of fields of view within the cloud atmosphere of the first and second optical fibers as projected through the collimator lens is greater than a predetermined threshold.

A further embodiment of any of the foregoing systems, the collimator lens can be configured to be rotatable.

A further embodiment of any of the foregoing systems, wherein the numerical apertures of the transmission end of the first optical fiber and the reception end of the second optical fiber can be each greater than a predetermined threshold.

A further embodiment of any of the foregoing systems, wherein the predetermined threshold is about 0.25, 0.30, 0.35 or about 0.5.

A further embodiment of any of the foregoing systems, wherein the laser diode is a first laser diode, the pulse of optical energy is a first pulse of optical energy of a first wavelength, the projection end is a first projection end, the reception end is a first reception end, and the detector is a first detector. The system can further include a second laser diode configured to generate a second pulse of optical energy of a second wavelength different from the first wavelength. The system can further include a third optical fiber configured to transmit the second generated pulse of optical energy and to divergently project, from a second projection end, the second transmitted pulse of optical energy over a third field-of-view determined by a third numerical aperture of the second projection end. The system can further include a fourth optical fiber having a reception end aligned proximate and substantially parallel to the second transmission end of the third optical fiber. The fourth optical fiber can be configured to receive a portion of the second projected pulse of optical energy reflected by the cloud atmosphere from within a fourth field of view determined by a fourth numerical aperture of the second reception end. The fourth field-of-view can include second narrow-field and second wide-field reception volumes of the cloud atmosphere. The second narrow-field reception volume can correspond to locations within the cloud atmosphere from which optical energy can be directed through the collimating lens and received by the fourth optical fiber. The second wide-field reception volume can correspond to locations within the cloud atmosphere from which optical energy can be received by the fourth optical fiber not through the collimating lens.

A further embodiment of any of the foregoing systems can further include a second detector configured to detect a portion of the second pulse of optical energy backscattered by the cloud atmosphere.

A further embodiment of any of the foregoing systems can further include an optical filter aligned with the collimating lens.

A further embodiment of any of the foregoing systems, wherein the optical filter is configured to transmit optical of the first wavelength and to absorb optical of the second wavelength.

Some embodiments relate to a method for measuring cloud parameters. The method includes generating a pulse of optical energy. The method includes diverging the generated pulse of optical energy over a solid angle greater than a predetermined threshold. The method includes collimating a portion of the divergent pulse of optical energy and projecting the collimated portion into a first projection volume of a cloud atmosphere. The method includes projecting an uncollimated portion of the divergent pulses of optical energy into a second projection volume of the cloud atmosphere. The method includes receiving optical energy from a first reception volume of the cloud atmosphere, the first reception volume intersecting the first projection volume. The method includes receiving optical energy from a second reception volume of the cloud atmosphere, the second reception volume intersecting the second projection volume. The method also includes detecting and generating a signal indicative of combined collimated and uncollimated portions backscattered by the cloud atmosphere from within the intersections of the first and second projection volumes and the first and second reception volumes, respectively.

The method of the preceding paragraph can optionally include, additionally and/or alternatively, any one or more of the following features, configurations and/or additional components:

A further embodiment of the foregoing method can further include calculating, based on the generated signal, a metric of SLDs.

A further embodiment of any of the foregoing methods can further include controlling a parameter of the collimated portion of the divergent pulses of optical energy projected into the cloud atmosphere.

A further embodiment of any of the foregoing methods, wherein controlling the parameter of the collimated portion of the divergent pulses of optical energy projected into the cloud atmosphere can include controlling a sampling volume of the collimated portion, wherein the sampling volume of the collimated portion is the intersections of the first projection volume and the first reception volume.

A further embodiment of any of the foregoing methods, wherein controlling the sampling volume of the cloud atmosphere can include controlling a relative orientation of a collimating lens with respect to a geometric alignment associated with projection and detection of the collimated portion.

A further embodiment of any of the foregoing methods, wherein the calculated metric can be a size and/or density of SLDs.

A further embodiment of any of the foregoing methods, wherein generating a pulse of optical energy can include generating a first pulse of optical energy having a first wavelength, the method further comprises. The method can also include generating a second pulse of optical energy having a second wavelength.

A further embodiment of any of the foregoing methods can further include filtering the generated first and second pulses of optical energy.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for measuring cloud parameters, the system comprising:
   a laser diode configured to transmit the generated a pulse of optical energy;
   a first optical fiber configured to transmit the generated pulse of optical energy and to divergently project, from a projection end, the transmitted pulse of optical energy over a first field-of-view determined by a first numerical aperture of the projection end;
   a collimating lens aligned within a subfield of the first field-of-view, the collimating lens configured to collimate a narrow-field portion of the divergently projected pulse of optical energy refracted by the collimating lens into a narrow-field projection volume of a cloud atmosphere, a wide-field projection volume of the cloud atmosphere corresponding to a portion of the projected pulse not collimated by the collimating lens;
   a second optical fiber having a reception end aligned proximate and substantially parallel to the transmission end of the first optical fiber, the second optical fiber configured to receive a portion of the projected pulse of optical energy reflected by the cloud atmosphere from within a second field of view determined by a second numerical aperture of the reception end, wherein the second field-of-view includes narrow-field and wide-field reception volumes of the cloud atmosphere, the narrow-field reception volume corresponding to locations within the cloud atmosphere from which optical energy is capable of being directed through the collimating lens and received by the second optical fiber, the wide-field reception volume corresponding to locations within the cloud atmosphere from which optical energy is capable of being received by the second optical fiber not through the collimating lens; and
   a detector configured to detect and generate a signal indicative of the portion of the projected pulse of optical energy backscattered by the cloud atmosphere and received by the second optical fiber.

2. The system of claim 1 further comprising:
   a processor configured to calculate, based on the generated signal, a metric of super-cooled large droplets.

3. The system of claim 1, wherein the calculated metric is a size and/or density of super-cooled large droplets.

4. The system of claim 3, wherein the collimator lens is a spherical lens.

5. The system of claim 3, wherein the collimator lens is a cylindrical lens.

6. The system of claim 5, wherein a relative orientation of the cylindrical lens with respect to an orientation of a juxtaposition of the transmission and reception ends, or the first and second optical fibers, respectively, is configured such that an intersection of fields of view within the cloud atmosphere of the first and second optical fibers as projected through the collimator lens is greater than a predetermined threshold.

7. The system of claim 6, wherein the collimator lens is configured to be rotatable.

8. The system of claim 1, wherein the numerical apertures of the transmission end of the first optical fiber and the reception end of the second optical fiber are each greater than a predetermined threshold.

9. The system of claim 8, wherein the predetermined threshold is about 0.25, 0.30, 0.35 or about 0.5.

10. The system of claim 1, wherein the laser diode is a first laser diode, the pulse of optical energy is a first pulse of optical energy of a first wavelength, the projection end is a first projection end, the reception end is a first reception end, and the detector is a first detector, the cloud conditions measurement system further comprising:
 a second laser diode configured to generate a second pulse of optical energy of a second wavelength different from the first wavelength; and
 a third optical fiber configured to transmit the second greatest pulse of optical energy and to divergently project, from a second projection end, the second transmitted pulse of optical energy over a third field-of-view determined by a third numerical aperture of the second projection end;
 a fourth optical fiber having a reception end aligned proximate and substantially parallel to the second transmission end of the third optical fiber, the fourth optical fiber configured to receive a portion of the second projected pulse of optical energy reflected by the cloud atmosphere from within a fourth field of view determined by a fourth numerical aperture of the second reception end, wherein the fourth field-of-view includes second narrow-field and second wide-field reception volumes of the cloud atmosphere, the second narrow-field reception volume corresponding to locations within the cloud atmosphere from which optical energy is capable of being directed through the collimating lens and received by the fourth optical fiber, the second wide-field reception volume corresponding to locations within the cloud atmosphere from which optical energy is capable of being received by the fourth optical fiber not through the collimating lens; and
 a second detector configured to detect a portion of the second pulse of optical energy backscattered by the cloud atmosphere.

11. The system of claim 10, further comprising an optical filter aligned with the collimating lens.

12. The system of claim 11, wherein the optical filter is configured to transmit optical of the first wavelength and to absorb optical of the second wavelength.

13. A method for measuring cloud parameters, the method comprising:
 generating, using an optical source, a pulse of optical energy;
 diverging, using a first optical fiber, the generated pulse of optical energy over a solid angle greater than a predetermined threshold;
 collimating, using a lens, a portion of the divergent pulse of optical energy and projecting the collimated portion into a first projection volume of a cloud atmosphere;
 projecting an uncollimated portion of the divergent pulses of optical energy into a second projection volume of the cloud atmosphere;
 receiving, using a second optical fiber, optical energy from a first reception volume of the cloud atmosphere, the first reception volume intersecting the first projection volume;
 receiving, using the second optical fiber, optical energy from a second reception volume of the cloud atmosphere, the second reception volume intersecting the second projection volume; and
 detecting and generating, using an optical detector, a signal indicative of combined collimated and uncollimated portions backscattered by the cloud atmosphere from within the intersections of the first and second projection volumes and the first and second reception volumes, respectively.

14. The method of claim 13, further comprising:
 calculating, based on the generator signal, a metric of super-cooled large droplets.

15. The method of claim 13, further comprising:
 Controlling a parameter of the collimated portion of the divergent pulses of optical energy projected into the cloud atmosphere.

16. The method of claim 15, wherein controlling the parameter of the collimated portion the divergent pulses of optical energy projected into the cloud atmosphere comprises:
 controlling a sampling volume of the collimated portion, wherein the sampling volume of the collimated portion is the intersections of the first projection volume and the first reception volume.

17. The method of claim 16, wherein controlling the sampling volume of the cloud atmosphere includes:
 controlling a relative orientation of a collimating lens with respect to a geometric alignment associated with projection and detection of the collimated portion.

18. The method of claim 13, wherein the calculated metric is a size and/or density of super-cooled large droplets.

19. The method of claim 13, wherein generating a pulse of optical energy comprises:
 generating a first pulse of optical energy having a first wavelength, the method further comprises:
 generating a second pulse of optical energy having a second wavelength.

20. The method of claim 19, further comprising:
 filtering the generated first and second pulses of optical energy.

* * * * *